US009845487B2

(12) United States Patent
Vágvölgyi et al.

(10) Patent No.: US 9,845,487 B2
(45) Date of Patent: Dec. 19, 2017

(54) SELECTIVE CHROMOGENIC MEDIUM

(71) Applicants: SZEGEDI TUDOMÁNYEGYETEM, Szeged (HU); SOLVO BIOTECHNOLÓGIAI ZRT, Szeged (HU)

(72) Inventors: Csaba Vágvölgyi, Szeged (HU); Ilona Pfeiffer, Szeged (HU); János Márky-Zay, Szeged (HU)

(73) Assignees: Szegedi Tudományegyetem, Szeged (HU); SOLVO Biotechnológiai ZRt., Szeged (HU)

( * ) Notice: Subject to any disclaimer, the term of this patent is extended or adjusted under 35 U.S.C. 154(b) by 0 days.

(21) Appl. No.: 14/780,651

(22) PCT Filed: Mar. 31, 2014

(86) PCT No.: PCT/IB2014/060323
§ 371 (c)(1),
(2) Date: Sep. 28, 2015

(87) PCT Pub. No.: WO2014/155369
PCT Pub. Date: Oct. 2, 2014

(65) Prior Publication Data
US 2016/0060678 A1 Mar. 3, 2016

(30) Foreign Application Priority Data
Mar. 29, 2013 (HU) .................................. 1300186

(51) Int. Cl.
C12Q 1/04 (2006.01)

(52) U.S. Cl.
CPC ......... *C12Q 1/045* (2013.01); *G01N 2333/39* (2013.01)

(58) Field of Classification Search
CPC .................................................... C12C 1/045
See application file for complete search history.

(56) References Cited

FOREIGN PATENT DOCUMENTS

| CN | 102517375 | 6/2012 |
| ES | 2 268 970 B1 | 2/2008 |
| JP | 2-31949 B2 | 7/1990 |
| WO | 00/73494 A1 | 12/2000 |
| WO | 00/73495 A1 | 12/2000 |

OTHER PUBLICATIONS

Lillie RD, American J of Public Health, 1943, 33:948-951.*
Rodrigues et al. J of Applied Microbiology, 2001, 90:588-599.*
Levine: "Levine EMB Agar (Eosin Methylenen-blue Lactose Agar acc to Levine)", Merck Microbiology Manual 12th Edition, 2007, pp. 325-326.
Barata et al.: "Ascomycetous yeast species recovered from grapes damaged by honeydew and sour rot." Journal of Applied Microbiology, 2008, vol. 104(4), pp. 1182-1191.
Cuoto et al.: "A simple cultural method for the presumptive detection of the yeasts Brettanomyces/Dekkera in wines", Lett Applied Microbiology, 2005, vol. 41(6), pp. 505-510.
Dmitri: "Tag Archives: Brettanomyces Staining the Berliner Weisse", Retrieved from the Internet:URL:https://bkyeast.wordpress.com/tag/brettanomyces/, 2011, pp. 1-3.
Dmitri: "Tag Archives: Looking at WYeast Berliner Weisse Brettanomyces and Saccaromyces", Retrieved from the Internet:URL:https://bkyeast.wordpress.com/tag/brettanomyces/, 2011, pp. 1-3.
Loureiro et al.: "Spoilage yeasts in the wine industry", Int J Food Microbiology, 2003, vol. 86(1-2), pp. 23-50.
Márki-Zay et al.: "Development and Evaluation of Methods for the Detection of Brettanomyces in Wine", Magyar Mikrobiológiai Társaság, 2010, pp. 58-59.
Renouf et al.: "Development of an enrichment medium to detect Dekkera/Brettanomyces bruxellensis, a spoilage wine yeast, on the surface of grape berries", Microbial Research, 2007, vol. 162(2), pp. 154-167.
Schuller et al.: "A Differential Medium for the Enumeration of the Spoilage Yeast Zygosaccharomyces bailii in Wine", J Food Protection, 2000, vol. 63(11), pp. 1570-1575.
Van Der Walt et al.: "The Wine Yeasts of the Cape", Antonie van Leeuwenhoek, vol. 26, 1960, pp. 292-296.
Weld: "Candida Albicans Rapid identification in Pure Cultures with Carbon Dioxide on Modified Eosin-Methylene Blue Medium", A.M.A. Archives of Dermatology and Syphilology,1952, vol. 66(6), pp. 691-694.

* cited by examiner

Primary Examiner — Bin Shen
(74) Attorney, Agent, or Firm — Jason D. Voight

(57) ABSTRACT

The invention deals with chromogenic media which are suitable for the selective growth and identification of one or more species of yeast.
The subject of the invention is the method that enables us to identify and determine the cell count of *Brettanomyces/Dekkera* and *Zygosaccharomyces* yeasts. Besides, the subjects of invention are also the use of the method in wine and/or food industry and the stocks for conducting the experiment.

19 Claims, 1 Drawing Sheet

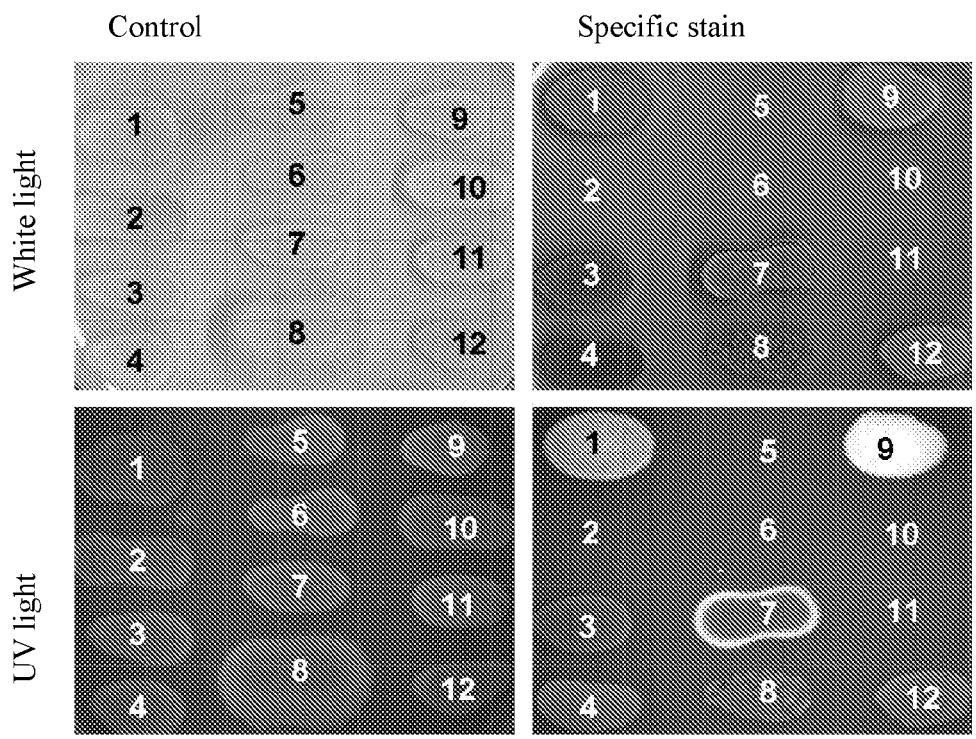
1. FIGURE: Identifying wild yeasts next to winemaking yeasts on selective medium
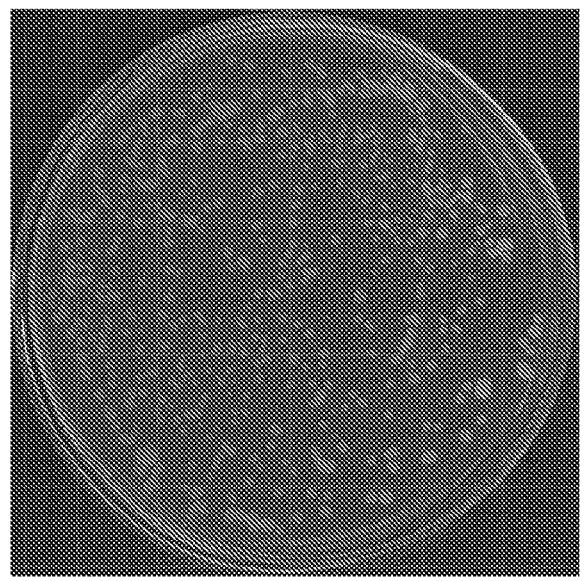
2. FIGURE: Colonies of *Brettanomyces* from vinous medium, on a selective, painted medium

SELECTIVE CHROMOGENIC MEDIUM

This is the national stage of International Application PCT/IB2014/060323, filed Mar. 31, 2014.

FIELD OF THE INVENTION

The invention relates to chromogenic media suitable for the selective growth and detection of one or more selected yeast species.

Preferably, the invention relates to methods suitable for the detection of yeast species of *Brettanomyces/Dekkera* and *Zygosaccharomyces* and for the determination of the cell count of said yeasts. The invention further relates to the use of said method in oenological and/or food industry processes and the media and kits necessary for performing the examination.

BACKGROUND OF THE INVENTION

The invention is suitable for the detection of the yeast species described herein from theoretically any kind of sample, preferably from a foodstuff, a food processing intermediate or a food raw material.

The selective detection and separation of yeast species having a role in beer and wine production that are in many cases detrimental, from wild yeast species is of particular significance.

Loureiro V and Malfeito-Ferreira M. [Spoilage yeasts in the wine industry. Int J Food Microbiol. 2003; 86(1-2):23-50.] give a detailed summary about microbiological problems caused by yeasts that are present in wine. The authors of the publication talk about methods that are presently known for detecting yeasts that cause deterioration in food, and analyze factors that help the colonization of yeasts on grapes and in wine.

Depreciation of wine that are originated in microbiological reasons cause a serious loss worldwide, affecting wine in premium categories, that are being matured in a wood barrel, even harder.

As this problem has a huge economic significance, procedures that recognize the presence and multiplication of harmful microorganisms on time are extremely important. With the help of these, the infestation can be prevented, or the intervention to lower the extent of deterioration can be done targetedly.

The majority of microorganisms that have a role in the creation of wine get into the process from the grapes or the wine-making equipment.

The species composition and the number of cells of the microflora change depending on the circumstances, the number of bacteria is infinitesimal, yeasts dominate. Among the yeasts, apart from the cultured (noble) strain of *Saccharomyces* there are many wild yeasts present, that dominate the fermenting medium for a long time. Among the wild yeasts, the genera of *Brettanomyces/Dekkera* and the *Zygosaccharomyces* tolerate high level of alcohol concentration relatively well and are resistant of the usual wine making procedures, therefore if they proliferate during the maturation of the wine it can cause the deterioration of it.

The genera of *Zygosaccharomyces*, especially the *Zygosaccharomyces bailii* can generate undesirable secondary fermentation and the formation of an adverse aroma in wines with residual sugar content, but at the same time they have a very important role in commencing the fermentation of high sugar content must and in fermenting must with inappropriate glucose: fructose proportion.

There is an adverse phenol-like character (the so called "brettyness") that is caused by the metaboism byproduct of the species of *Brettanomyces* (mainly the *B. bruxellensis*) particularly during the production of red wine and as a consequence there is a significant decrease in quality and price. These non desirable components of flavor were described by sensory evaluations as "disinfectant", "bretty", "leather", "wet dog", "rancid", "sweaty horse", "ordure", "stall" and "animal character". The compounds arisen by the influence of *Brettanomyces*, in small quantities can contribute to the complexity of the wine (mild animality), however, above a certain number of cells the presence of the *Brettanomyce* is non-desirable. Their proliferation at an early stage of maturation can be prevented with carbon monoxide treatment, to which these yeasts are relatively sensitive. Although the sulphurization itself can influence the smell of the wine in a disadvantageous way and suppress the development, therefore the treatment has to be targeted. The condition of targeted intervention is the early identification of the presence of *Brettanomyces* in the maturing wine, when the number of these microorganisms and the concentration of their metabolism products are still low.

For this, we can use a number of analytical methods (ELISA, molecular biology methods, flow cytometry, culturing, chromatography methods), but most of them require special equipment and knowledge, furthermore they are very time consuming and sumptous, because in the medium there are a large number of other microorganisms that makes demonstrability very difficult.

For example, Cocolin and his co-workers [Molecular Detection and Identification of B*rettanomyces/Dekkera bruxellensis* and *Brettanomyces/Dekkera anomalus* in Spoiled Wines. Appl Environ Microbiol. 2004; 70(3): 1347-1355.] created a PRC-RFLP test for the identification of *Brettanomyces bruxellensis* and *Brettanomyces anomalus*. The key of their method is that different patterns for the two species are obtained, when a DNA fragment that was propagated during the PCR reaction is digested with restriction enzyme. The method is highly sensitive, and is suitable for detecting and separating two *Brettanomyce* species, however, it requires special lab equipment and it is relatively costly.

Phister and Mills Meal-Time PCR Assay for Detection and Enumeration of *Dekkera bruxellensis* in Wine. Applied and Environmental Microbiology. 2003; 69(147430-74341 used the RT-PCR method for identifying the *Dekkera (Brettanomyces) bruxellensis* in wine. The method is very sensitive (it is able to make a detection in a concentration of 1 cell/ml) and selective, but it is even more expensive than the traditional PCR, the equipment costs are also high and its use requires appropriately qualified personnel.

Stender and his colleagues [Identification of *Dekkera bruxellensis (Brerranomyces)* from wine by fluorescence in situ hybridization using peptide nucleic acid probes. Appl. Environ. Microbiol. 67:938-941 (2001)] detected *Dekkera (Brettanomyces) bruxellensis* from wine, Connell and his colleagues [Rapid Detection and Identification of *Brettanomyces* from Winery Air Samples Based on Peptide Nucleic Acid Analysis. Am. J. Enol. Vitic. 2002; 53(4): 322-24] detected *Brettanomyces* strains from the air of cellars with chemiluminescence in situ hybridization method (with the application of peptide nucleic acid probe). The method is highly sensitive, but is based on culturing, therefore it is time consuming and requires qualified workers, additionally, the cost of the tests are significant.

Mitrakul and his colleagues [Discrimination of *Brettanomyces/Dekkera* yeast isolates from wine by using various DNA fingerprinting methods. Food Microbiol. 1999 16 3-14.] used the RAPD-PCR method for the identification of *Brettanomyces/Dekkera* strains. This method is suitable for species and strain identification, but its condition is having a special instrument (PCR). The authors used it in combination with other identification methods, which were based on culturing and physiological tests, therefore the assay also became time consuming.

Ibeas and his colleagues [Detection of *Dekkera-Brettanomyces* Strains in Sherry by a Nested PCR Method. Appl. Environ. Microbiol. 1996, 62(3) 998-1003] identified *Brettanomyces/Dekkera* strains in sherry, with "nested" PCR. This method is highly sensitive, it does not require growing the strains, therefore it gives a quick, reliable result in 10 hours. Although it requires special equipment, and remains of sherry in the sample block the reaction, thus we can get a false result.

The Oeno Yeast Kit (Partec) identification is a fluorescent detection method, based on flow cytometry, that detects metabolically active yeast cells. Similarly to other cytometric procedures, this method is not specific to *Brettanomyces/Dekkera species*, therefore it can only be used in wine samples that are in the phase of maturing, when the presence of other yeasts are not probable. The test is expensive and needs special instruments.

To sum up, the advantage of molecular methods are selectivity and quickness, the advantage of instrumental methods are accuracy and quickness. Their disadvantage is that they require special and expensive instruments, the reaction is quite costly and the implementation and evaluation require qualified personnel. The common disadvantage of procedures of molecular biology is that if they identify one or two species, other species that can trigger deterioration of wine and food stay hidden.

The solution to this problem is using a medium, that is selective to the species of *Brettanomyces/Dekkera* and/or *Zygosaccharomyces*. The significant benefit of this medium is that using it does not require special equipment, neither microbiologist, nor analytical qualifications, and the examination can be carried out and evaluated in a wine cellar by an oenologist. A disadvantage of this technique that the selectivity of the medium is limited, therefore other microorganisms, e.g. colonies of wild yeast might appear (false positive result).

Renouf V. and Lonvaud-Funel A. [Development of an enrichment medium to detect *Dekkera/Brettanomyces bruxellensis*, a spoilage wine yeast, on the surface of grape berries. Microbiol Res. 2007; 162(2):154-67.] created a selective medium and with that, the species of *Dekkera/Brettanomyces* can be enriched, thus the procedure of indentification can be made sensitive.

Barata A. and his colleagues [Ascomycetous yeast species recovered from grapes damaged by honeydew and sour rot. Journal of Applied Microbiology, 2008 104(4) 1182-1191.] rose the alcohol content and used cycloheximide only as a source of carbon, thus assuring that their medium is selective for species of *Dekkera/Brettanomyces*.

Schuller D. and his colleagues C. [A differential medium for the enumeration of the spoilage yeast *Zygosaccharomyces bailii* in wine. J Food Prot. 2000 63(11):1570-5.] created a medium that serves the selective culturing of *Zygosaccharomyces bailii*. With the proper adjustment of the concentration of formic acid and glucose they made the medium so selective, that only the *Z. bailii* caused a pH drift to alkaline direction, which resulted in a change of colour of the medium.

The aim of Hocking A D. [Media for preservative resistant yeasts: a collaborative study. Int J Food Microbiol. 1996 29(2-3):167-75] was creating a medium that is most suitable for identifying yeast that is resistant to preservatives in food. According to the publication, they authors examined 5 media, from which 3 were selective. Two out of 3 were made selective by adding acetic acid, while the third medium was a ZBM (*Zygosaccharomyces bailii*) medium, which contained tripan blue paint. When comparing the efficacy of the media, the ZBM medium appeared to be adequately selective for *Z. bailii*, however, it was less suitable for counting because its growing inhibition effect.

By applying the above mentioned methods, media can be made selective for growing yeasts. An additional task is to identify the given yeast species, which in case of wild yeast is often done by scent sample, by adding a compound to the medium, e.g. p-coumaric acid, which transforms the yeast to a distinctive smelling compound.

Couto J. A. and his colleagues [A simple cultural method for the presumptive detection of the yeasts *Brettanomyces/Dekkera* in wines. Left Appl Microbiol. 2005 41(6):505-10.] presents an easy and reliable method in their publication for identifying the *Brettanomyces/Dekkera* yeasts. The base of their method is utilizing selective medium, which contains glucose, cycloheximide, chloramphenicol and p-coumaric acid. The presence of yeasts are evaluated by turbidity and scent.

Rodrigues N, and his colleagues [Development and use of a new medium to detect yeasts of the genera *Dekkera/Brettanomyces*. J Appl Microbiol. 2001 90(4):588-99.] developed a selective medium as well, for identifying species of *Dekkera/Brettanomyces* in an environment connected to wine making. They ensured the selectiveness of the medium by adding ethanol and cycloheximide. They proved the identification of acid producing strains by adding bromocresol green. Adding p-coumaric acid ensured the identification of *Dekkera/Brettanomyces* strains based on scent samples.

During the method applied by Lebrun Labs (Easy Blue *Brettanomyces* Test Kit), the selective medium that blocks the growth of most yeasts discolours from the effect of acids produced by microbes (pH change). Furthermore, the *Dekkera/Brettanomyces* colonies produce a distinctive smelling, volatile compound from the p-coumaric acid in the medium, whose perception happens by smelling it, so it requires experience and/or a comparative scent sample. Although this method does not require qualification or special instruments, it has its disadvantages: the medium is not absolute selective, which can lead to false positive results.

During the supplementary usage of p-coumaric acid, the metabolite it formulates [4-ethylfenol (4-EP), 4-ethylguaiacol (4-EG), isovaleric acid] has a smell that is typical of *Brettanomyces/Dekkera* yeasts, whose identification requires experience and/or scent sample. Taking a scent sample means opening the Petri dish again and again, which become a potential source of infection themselves.

Therefore, according to the technical knowledge, there were proposals for solutions, where the mentioned species of wild yeast were identified in a chromogenic medium, based on a reaction that was accompanied by discolouration.

Loureiro V, Malfeito-Ferreira M. ["Spoilage yeasts in the wine industry." Int J Food Microbiol. 2003 86(1-2):23-50.] have a detailed, in-depth summary where they discuss the colony of yeasts on grapes and in wines, as well as mentioning the industrial identification techniques. They present the components that must be found in general media that are for identifying yeasts, and in relation to these they mention indicators that are used in these media: bromocresol green and bromphenol blue.

In the international publication no. WO0073494 (A1) Leao Cecilia and her colleagues describe media that are eligible for identifying species of *Zygosaccharomyces*, such as *Zygosaccharomyces bailii* and *Zygosaccharomyces bisporus*, from wine and other food. The medium is made of a general mineral medium, that is supplemented with vitamins and trace elements, glucose and formic acid as sources of carbon, acid base indicator and optionally with antibiotics. Here, the indicator is mostly bromocresol green.

On the blue selective medium, distributed by Millipore, we experience the discolouration around the *Brettanomyces* colonies, due to the acid they produce.

The solution (inventors: Loureiro Virgilio Borges and colleagues. "Culture medium for detection of *Dekkera* and *Brettanomyces*") that was disclosed in the patent application, published under the number of EP1185686(A1) (it corresponds to the international publication no. WO2000073495A1), relates to a method and use of a general medium for identifying *Dekkera* and *Brettanomyces* yeasts, and determining their cell counts. According to the method, the following are added to the medium: nutrients; nonfermentable energy source, mainly ethanol; p-coumaric acid; acid base indicator, mainly bromocresol green; cycloheximide for blocking the growth of yeasts and antibiotics for blocking the growth of bacteria, chloramphenicol or oxytetracycline. The medium shows a distinctive discolouration as an effect of cultured (noble) colonies of *Dekkera* and *Brettanomyces* strains. The degree of discolouration changes depending on the growth pattern as an effect of decreasing pH. Furthermore, during culturing a distinctive, phenol-like aroma develops after a few days of incubation, which is easy to identify. The invention can be applied well in food industry.

In publication No. ES2268970(A1) Velazquez P. E. et al ("Yeasts detection culture medium comprises glucose mixed with buffer microorganism and bacterial growth inhibitors and e.g. a nitrogen source") a medium suitable for the detection of yeasts has been taught, where the medium comprises glucose as carbon source, a calcium carbonate buffer, active agents capable of inhibiting the growth of different microorganisms and bacteria, nitrogen sources and a pH indicator which is actually neutral red. The medium is capable of detecting the *Brettanomyces/Dekkera bruxellensis* in foods and drinks. The identification is based on the acetic acid odour of the medium and on the appearance of transparent lines around the *Dekkera/Brettanomyces* yeast colonies present in the medium.

The Japanese patent application JP56106588 discloses a method for the production of a biological culture medium which contains methoxylated pectin and which is formed by admixing lactose (5 g), eosine Y (0.5 g), methylene blue (0.065 g), low methoxylated pectin (25 g) and deionized water (1 l) in the presence of agar-agar. The resulted mixture is sterilized, its pH is adjusted to 7.1 with sodium phosphate, and in a Petri dish a gel is poured from the resulted mixture. The culture medium is used for culturing yeasts, bacteria, microorganisms and fungi. The inventors do not have any knowledge about whether the medium is suitable for detecting yeast species, particularly *Dekkera/Brettanomyces* yeast colonies on the basis of colour change.

The above mentioned methods, that are based on culturing, can be conducted with minimal previous experience and they are cheap. In the case of the present methods, the identification is based mostly on the colour change of the indicator, for example, the organic acids produced by the *Brettanomyces* cause the acidification of the pH of the medium and thus the change of colour of the indicator. The selectivity of the methods were usually limited, therefore they were unable to distinguish certain wild yeasts from one another. The object of the invention is aimed to develop a medium and a selective culturing method which is more reliable and more easily estimable than previous ones and by the application of which, specific yeast colonies can be visually identified and unambiguously distinguished and separated from other microorganisms able to grow on the medium and which are relatively less problematic in the aspect of oenology.

SHORT DESCRIPTION OF THE INVENTION

The invention is based on the finding that the different metabolites of yeasts cause differentiated changes of colour of certain staines, i.e. different groups of yeasts cause different colour reactions in the medium of the invention and are thereby selectively detectable.

The invention relates to a chromogenic and preferably selective medium suitable for the detection and growth of one or more yeast(s), optionally of harmful (detrimental) yeast, comprising a nutrient suitable for the feeding and/or growing of yeast, including at least or preferably the one or more yeast species to be detected, an agent capable of inhibiting the growth of other microorganisms, preferably of other yeasts, more preferably of *Saccharomyces* species, preferably in a concentration capable of inhibiting said growth, and a chromogenic stain, wherein the chromogenic stain is the combination of the following dyes, said combination being chromatic in visible light:

one or more types of substituted and/or unsubstituted bis-3,7 diaminophenothiazines, and one or more types of substituted fluoresceins.

Preferably, the bis-3,7 diaminophenothiazine dye of formula I in the medium of the invention has the chemical structure

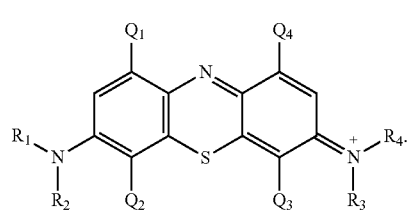

I wherein

R1, R2, R3 and R4 are independently H, methyl or ethyl, preferably H or methyl,

Q1, Q2, Q3 and Q4 are independently H, C1-4 alkyl, halogen, pseudohalogen, —NO or —NO$_2$, preferably H, methyl or ethyl, most preferably H, or the soluble salt thereof, and the chemical structure of the substituted fluorescein dye of formula II is

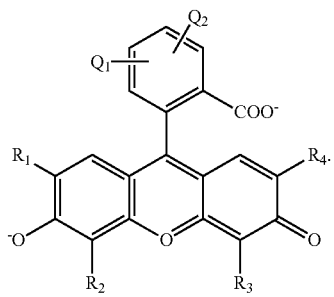

II wherein

R1, R2, R3 and R4 are independently halogen, pseudohalogen, —NO or —NO$_2$,

Q1 and Q2 are H, C1-4 alkyl, C1-4 alkoxy, halogen, pseudohalogen, —NO vagy —NO$_2$, 5- or 6-member heterocycle or Q1 and Q2 together form a 5- or 6-member heterocycle, in which case Q1 and Q2 are situated on adjacent C atoms, or the soluble salt thereof.

Preferably, the substituted or unsubstituted bis-3,7 diaminophenothiazine is selected from the group consisting of: methylene blue, methylene violet, azure stains, such as Azure A, Azure B and any mixtures thereof. Preferably, the medium of the invention contains at least two substituted or unsubstituted bis-3,7 diaminophenothiazine compounds selected from the group consisting of: methylene blue, methylene violet, Azure A, Azure B, most preferably selected from methylene blue, Azure B, Azure A, Azure C, thionine.

Preferably, the substituted fluorescein is selected from the group consisting of: Eosin Y, Eosin B and any mixtures thereof. Preferably, the substituted fluorescein is Eosin Y.

Preferably, the chromogenic stain comprises at least two types of bis-3,7 diaminophenothiazines having different degrees of methylation, preferably the mixture of methylene blue and Azure B. In a preferred embodiment the bis-3,7 diaminophenothiazines of two different degrees of methylation (e.g. two of methylene blue, Azure B, Azure A, Azure C, thionine defined herebelow, particularly methylene blue and Azure B) have molar amounts that are at most 50% or 30%, preferably at most 20% or 10% different relative to the component that is present in smaller amount. Most preferably, the chromogenic stain is a mixture of methylene blue and Azure B in a ratio of essentially 1:1 and of Eosin Y (Azure II eosinate).

Most preferably, the chromogenic stain is a mixture of the substituted or unsubstituted bis-3,7 diaminophenothiazine and the substituted fluorescein, preferably in a ratio of from 1.5:1 to 1:1. Most preferably, the substituted or unsubstituted bis-3,7 diaminophenothiazine is a mixture of methylene blue and Azure B, preferably in a ratio of essentially 1:1. More preferably, the chromogenic stain in the selective and chromogenic medium is Azure II eosinate.

In a preferred embodiment, the molar amounts of the at least one type of substituted or unsubstituted bis-3,7 diaminophenothiazine dye and the at least one type of substituted fluorescein dye are at most 50% or 30%, preferably 20% or 10% different relative to the amount of the component that is present in smaller amount.

Most preferably, the culture medium of the invention comprises multiple types of substituted or unsubstituted bis-3,7 diaminophenothiazine dyes, wherein R1, R2, R3 and R4 in general formula I are H, methyl or ethyl, preferably H or methyl so that the substituents R1, R2, R3 és R4 are different in the different dyes. Most preferably, the 3,7 diaminophenothiazine dye of the invention is a mixture of compounds with different degrees of methylation. Most preferably, R1, R2, R3 and R4 are H or methyl, and the bis-3,7 diaminophenothiazine component dyes are different in the degree of methylation.

Accordingly and preferably, methylene blue and the demethylated intermediers thereof or the mixture thereof may also be used in the stain, selected from:

a 3,7-bis(dimethylamino)-phenothiazin-5-ium salt, preferably acetate or chloride (methylene blue), a N-methyl,N',N'-dimethylphenothiazin-5-ium-3,7-diamine salt, preferably acetate or chloride (Azure B), a N',N'-dimethylphenothiazin-5-ium-3,7-diamine salt, preferably acetate or chloride (Azure A: CAS 531 533), a N-methylphenothiazin-5-ium-3,7-diamine salt, preferably acetate or chloride (Azure C), a Phenotiazin-5-ium-3,7-diamine salt, preferably chloride or acetate (thionine).

Most preferably, the stain comprises a mixture of Azure B and methylene blue.

Preferably, the invention relates to a chromogenic and preferably selective medium suitable for the selective growth and detection of one or more yeast(s) selected from:

a yeast species of the *Brettanomyces* and/or *Dekkera* genera, a yeast species of the *Zygosaccharomyces* genus, a yeast species of the *Lachancea* genus, preferably at least a yeast species of the *Brettanomyces* and/or *Dekkera* genera, and comprising a nutrient suitable for the nutrition and/or growth of yeasts including at least or preferably the one or more yeast species to be detected, an agent capable of inhibiting the growth of other microorganisms, preferably of other yeasts, more preferably of *Saccharomyces* species, preferably in a concentration capable of inhibiting said growth, and a chromogenic stain, wherein the chromogenic stain is the combination of the following dyes, said combination being chromatic in visible light:

one or more types, preferably at least two types, preferably two types of substituted and/or unsubstituted bis-3,7 diaminophenothiazines selected from:

a 3,7-bis(dimethylamino)-phenothiazin-5-ium salt, preferably acetate or chloride (methylene blue), a N-methyl,N',N'-dimethylphenothiazin-5-ium-3,7-diamine salt, preferably acetate or chloride (Azure B), a N',N'-dimethylphenothiazin-5-ium-3,7-diamin salt, preferably acetate or chloride (Azure A), a N-methylphenothiazin-5-ium-3,7-diamine salt, preferably acetate or chloride (Azure C), a Phenotiazin-5-ium-3,7-diamine salt, preferably chloride or acetate (thionine), and one or more types of substituted fluoresceins selected from: eosin dyes, preferably Eosin B and Eosin Y.

In a preferred embodiment the selective and chromogenic medium comprises a gelling agent and is formulated as:

solid powder, gelled culture medium and preferably the medium is in a pre-prepared, ready to use form, preferably in solid and/or gel form, most preferably being pre-poured on plates.

Most preferably, the agent inhibiting the growth of *Saccharomyces* species is a chemotherapeutic agent or an antibiotic, preferably cycloheximide According to a further aspect, the invention relates to the use of the chromogenic medium of the invention for the detection or qualitative or quantitative determination of one or more yeast(s) from a foodstuff, a food processing intermediate, and/or a food raw material, preferably an agricultural product, the yeast selected from: a yeast of the *Brettanomyces* and/or *Dekkera* genera, a yeast of the *Zygosaccharomyces* genus and/or a yeast of the *Lachancea* genus.

In a preferred embodiment a yeast of the *Brettanomyces* and/or *Dekkera* genera is detected, said yeast is preferably selected from the group consisting of *Brettanomyces bruxellensis*, *Brettanomyces anomalus*, *Brettanomyces custersianus*, *Brettanomyces naardenensis*, and *Brettanomyces maims*.

In a preferred embodiment a yeast species of the *Zygosaccharomyces* genus is detected, wherein said yeast is preferably *Zygosaccharomyces bailii*.

In a preferred embodiment a yeast species of the *Lachancea* genus is detected, wherein said yeast is preferably *Lachancea fermentatii*.

Preferably, the invention relates to the use of the following chromogenic and selective medium for the detection or qualitative or quantitative determination of one or more yeast(s) from a foodstuff, a food processing intermediate, and/or a food raw material, wherein the foodstuff is preferably a foodstuff prepared by fermentation, particularly wine, said yeast being selected from a yeast of the *Brettanomyces* and/or *Dekkera* genera, a yeast of the *Zygosaccharomyces* genus and/or a yeast of the *Lachancea* genus, preferably at least a yeast of the *Brettanomyces* and/or *Dekkera* genera, wherein the medium that is chromogenic and selective is suitable for the selective growth and detection of said one or more yeast(s), and said medium contains a nutrient suitable for the nutrition and/or growth of yeasts including at least or preferably the one or more yeast species to be detected, an agent capable of inhibiting the growth of other microorganisms, preferably of other yeasts, more preferably of *Saccharomyces* species, preferably in a concentration capable of inhibiting said growth, and a chromogenic stain, wherein the chromogenic stain is the combination of the following dyes said combination being chromatic in visible light:

one or more type(s), preferably at least two types, preferably two types of substituted and/or unsubstituted bis-3,7 diaminophenothiazines selected from:

a 3,7-bis(dimethylamino)-phenothiazin-5-ium salt, preferably acetate or chloride (methylene blue), a N-methyl,N',N'-dimethylphenothiazin-5-ium-3,7-diamine salt, preferably acetate or chloride (Azure B), a N',N'-dimethylphenothiazin-5-ium-3,7-diamin salt, preferably acetate or chloride (Azure A), a N-methylphenothiazin-5-ium-3,7-diamine salt, preferably acetate or chloride (Azure C), a Phenotiazin-5-ium-3,7-diamine salt, preferably chloride or acetate (thionine), and one or more type(s) of substituted fluoresceins selected from: eosine dyes, preferably Eosin B and Eosin Y.

In the use according to the invention preferably, when the colony is pink and/or strongly fuorescent under UV light, it is considered to be the detection of a yeast species or multiple yeast species of the *Brettanomyces* and/or *Dekkera* genera, preferably, when the colony is blue and optionally faintly fuorescent under UV light, it is considered to be the detection of a yeast species of the *Zygosaccharomyces* genus, preferably *Zygosaccharomyces bailii*, preferably, when the colony is greenish blue with a pink edge and/or is faintly fluorescent under UV light with the edge strongly fluorescent under UV light, it is considered to be the detection of a yeast species of the *Lachancea* genus, preferably *Lachancea fermentatii*.

Preferably, the foodstuff prepared by fermentation according to the invention is preferably wine or beer, particularly preferably red wine.

According to a further aspect, the invention relates to a method for the detection or qualitative or quantitative determination of one or more yeast(s) selected from the group below, from a foodstuff, a food processing intermediate, and/or a food raw material, the method comprising the following steps:

providing the medium of the invention, in particular a medium selected from the media defined supra, obtaining a sample from a foodstuff, a food processing intermediate and/or a raw food material, wherein the foodstuff is preferably a foodstuff prepared by fermentation, particularly wine, preparing the sample to add to the medium, optionally filtering and/or concentrating and/or enriching the sample in microorganisms, plating the sample or suitable part thereof on the medium, incubating the medium under conditions suitable for the culturing of the yeast species, until colonies are obtained, detecting the yeast species by the discolouration of said colonies.

Preferably, said yeast is a yeast of the *Brettanomyces* and/or *Dekkera* genera.

Preferably, said yeast is a yeast or yeast species of the *Zygosaccharomyces* genus.

Preferably, said yeast is a yeast or yeast species of the *Lachancea* genus.

Preferably, when the colony is pink and strongly fluorescent under UV light, it is considered to be the detection of a yeast or multiple yeast species of the *Brettanomyces* and/or *Dekkera* genera.

Preferably, when the colony is blue and optionally faintly fluorescent under UV light, it is considered to be the detection of a yeast species of the *Zygosaccharomyces* genus, preferably *Zygosaccharomyces bailii*.

Preferably, when the colony is greenish blue with a pink edge and/or is faintly fluorescent under UV light with the edge strongly fluorescent under UV light, it is considered to be the detection of a yeast species of the *Lachancea* genus, preferably *Lachancea fermentatii*.

According to a preferred embodiment, the number of the colonies is provided relative to the amount of the original sample, preferably the volume or weight thereof, and therefore the method is quantitative.

Most preferably, the colonies and preferably the number of the colonies are evaluated under UV light, based on fluorescence.

In a preferred embodiment the foodstuff is a foodstuff prepared by fermentation, preferably beer or wine, preferably red wine, the food processing intermediate is malt, must, fermenting malt or must, and/or the food raw material is grape.

According to a preferred embodiment, the culture medium suitable for the culturing of said yeast is provided in a pre-prepared, ready to use form, preferably in solid or gel form, most preferably being pre-poured on plates.

According to a further aspect, the invention relates to a reagent kit for use in the method of the invention, containing the medium of the invention and means of preparing a gel culture medium thereof.

Definitions

In accordance with the taxonomical classification of *Brettanomyces/Dekkera* genus, first the anamorph (asexually reproducing) forms were identified and such forms were subsequently classified into the *Brettanomyces* genus. Later, the presences of sexually reproducing forms were also observed in certain species, which were classified into the *Dekkera* genus. The following species were identified as anamorph species: *Brettanomyces bruxellensis, Brettanomyces anomalus, Brettanomyces custersianus, Brettanomyces naardenensis,* and *Brettanomyces nanus,* while telemorph character was established with regard to two species: *Dekkera bruxellensis* and *Dekkera anomala.* However, later, it was verified by DNA tests that these two are identical with *Brettanomyces bruxellensis* and *Brettanomyces anomalus,* which actually represent their telemorph variations. Accordingly, in the description the professionally accepted "*Brettanomyces/Dekkera*" term is used, which generally includes any yeasts that are identified or taxonomically classified as members of these genus.

The *Brettanomyces/Dekkera* genus includes *B. anomalus, B. bruxellensis, B. claussenii, B. custersianus, B. lambicus, B. naardenensis* and *B. nanus* species.

In the description "medium" refers to any nutrient containing media suitable for feeding and growing yeast species and which can be prepared in solid, e.g. gel, form. The term "culture medium" refers to a medium which is solid, e.g. gel-like, and microorganisms are applied on the surface of culture medium.

"Yeasts" constitute a group of fungi which are eukaryote species having nucleus, generally one-celled, although under certain conditions some of their species are capable of forming pseudo or real mycelium. They reproduce via budding or via fission. Although in a broad sense, these species do not constitute a single phylogenetic category, they can generally be classified into two phyla (divisions), the *Ascomycetes* and the *Basidiomycetes*.

Preferably, one or more yeasts that can be detected according to the invention belong to the yeasts of the Ascomycota phylum, more preferably of the Saccharomycotina subphylum, more preferably of the Saccharomycetes class, highly preferably of the Saccharomycetaceae family.

The term "yeast" refers to yeast, yeast type or yeast category defined in a specific manner, preferably, to yeast that belongs to a definite taxonomical unit, particularly preferably to a definite genus or species.

In the description the term "yeast species" means any yeast known to have an expressly beneficial effect on the given fermentation process and which is appropriately characterized. Preferably, noble yeast is an established strain of a given yeast species. The term "harmful yeast species" or "harmful yeast" means any yeast, the presence of which or the presence of which above a given amount or concentration has a detrimental effect on the production of a given product prepared by fermentation.

"Product prepared by fermentation" means any product, preferably food products, for the preparation of which a yeast effect, preferably the conversion of carbohydrates to alcohol and carbon dioxide by the yeast, is necessary. Preferably, the product prepared by fermentation contains alcohol, i.e. is an alcoholic beverage, preferably beer or wine, highly preferably wine, more preferably red wine.

The word "contains" is no exclusionary in its meaning and allows for the addition or involvement of other properties or procedural steps to the content of the already listed properties or procedural steps.

In the context of the description the word "contains" can be limited to the expressions "it basically contains" and/or "in fact, it contains" which should be interpreted as "it contains" prescribed properties or prescribed procedural steps or components which are specified in some list, e.g. within the scope of the patient claim but in addition to these the presence of further properties, procedural steps, or components fundamentally not affecting any other objects described in the invention are also allowed.

The word "one" used in some of the definitions in the description and where the context so permits article "a" importing the singular can be deemed to carry the meaning of plural unless otherwise required by the context, unless, for example, the usage of "one" unambiguously refers to "one" as a numeral.

DESCRIPTION OF THE FIGURES

FIG. 1: Identification of wild yeasts along winemaking (noble) yeasts on selective medium The patterns assigned to sequence numbers are the following:

1: *Dekkera bruxellensis* CBS 73; 2: *Pichia membranifaciens* var. *membranifaciens* CBS 191; 3: *Zygosaccharomyces bailii* var. *bailii* CBS 4688; 4: *Zygosaccharomyces bailii* var. *bailii* CBS 4689; 5: *Zygosaccharomyces mellis* CBS 684; 6: *Zygosaccharomyces rouxii* CBS 441; 7: *Lachancea fermentati* CBS 707; 8: *Issatchekia orientalis* CBS 6799; 9: *Brettanomyces custersianus* CBS 4805; 10: *Saccharomyces cerevisiae* T-158C; 11: *Saccharomyces cerevisiae* S6; 12: *Schizosaccharomyces pombe*

FIG. 2: colonies of *Brettanomyces* from a vinous media, on a selective, coloured medium

DETAILED DESCRIPTION OF THE INVENTION

The present inventors unexpectedly found during the creation of the invention that if azure-II-eosinate or other chromogenic paint that contains chemically similarly structured molecules is added to a selective medium—which is suitable for growing yeast, but blocking the growth of *Saccharomyces*—then in the medium we get, we can identify *Brettanomyces* species among the appearing colonies, with the help of azure-II-eosinate.

Quite surprisingly, the present inventors observed the following:
1. On this medium, the *Brettanomyces* colonies are painted pink, which are visible for the eyes
2. The pink colonies are fluorescent in ultraviolet light, which confirms the separation of the species.

With the help of this method, the *Brettanomyces/Dekkera* colonies can be easily distinguished from other wild yeasts that are able to grow on a selective medium, by looking at them. The identification that is based on visibility, not only makes the identification process much easier, but it also does not require experience and scent samples, furthermore, it makes scenting samples unnecessary, which bears the possibility of spreading the infection. The reason why it is more specific to *Brettanomyces/Dekkera* species than other methods, is that it is able to identify other yeast species that are not winemaking (noble) yeasts, which (only) causes a problem in case of sweet wines with a higher residue of sugar.

We have also run the experiments using different azure and eosin dyes. All of the stains' colours changed with the increase of pH. Yet, these stains did not provide the previously experienced colour reaction and were not appropriate to distinguish the species of Brettanomyces/Dekkera from other, examined yeasts.

According to the invention, for getting the desired results, we need substituted or unsubstituted bis-3,7-diamino-phenothiazines together with the substituted derivatives of fluorescein.

There was a medium stain that was known before with the same components, eosin and methylene blue, but it was not used for identifying yeast contamination. For example, the United Kingdom publication no. GB1248197 [ABBOTT LAB (US), "Diagnostic method and apparatus for the detection of bacteria"] discloses an eosin methylene blue agar medium that contains lactose, however, identifying the yeasts in the reference are not based on eosin methylene blue medium. For our understanding, previously they used the azure-II-eosin for other purposes, mainly for colouring tissue samples.

According to the Japanese disclosure document no. JP56106588A they used eosin-Y (0.5 g, $7.23 \times 10^{-4}$ mol) and methylene blue (0.065 g, $2.03 \times 10^{-4}$ mol) in one medium only, however, the document does not provide any information about the different discolouration of the medium and/or the colonies as a result of growing different types of yeasts.

The chromogenic stain to be used according to the invention is therefore the combination of at least one type of substituted or unsubstituted bis-3,7 diaminophenothiazine stain and at least one type of substituted fluorescein stain. Preferably, the combination of the substituted or unsubstituted bis-3,7 diaminophenothiazine stain of formula I herebelow and the substituted fluorescein stain of formula II herebelow.

The chemical structure of the bis-3,7 diaminophenothiazine stain of formula I is

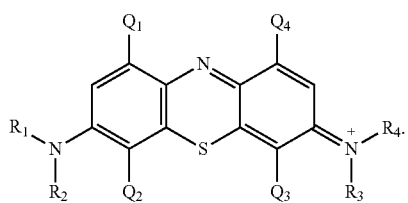

I wherein

R1, R2, R3 and R4 are independently H, methyl or ethyl, preferably H or methyl,

Q1, Q2, Q3 and Q4 are independently H, C1-4 alkyl, halogen, pseudohalogen, —NO or —$NO_2$, preferably H, methyl or ethyl, preferably H or methyl, most preferably H.

Preferably, the bis-3,7 diaminophenothiazine stain of formula I is present in a cationic form, such as a salt formed with an anion. The anion is preferably a halide ion, most preferably chloride ion. According to a variation, the anion is formed by the substituted fluorescent stain of formula II.

The chemical structure of the substituted fluorescent stain of formula II is

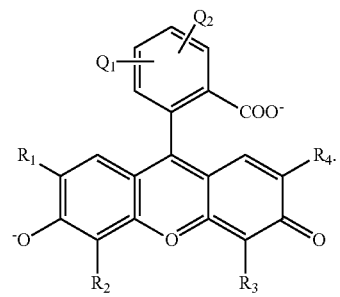

II wherein R1, R2, R3 és R4 are independently halogen, pseudohalogen, —NO or —$NO_2$, Q1 and Q2 are H, C1-4 alkyl, C1-4 alkoxy, halogen, pseudohalogen, —NO or —$NO_2$, 5- or 6-member heterocycle or Q1 and Q2 together form a 5- or 6-member heterocycle, in which case Q1 and Q2 are situated on adjacent C atoms.

Preferably, R1 and R4 are halogen, more preferably Br or —$NO_2$.

Preferably, R2 and R3 are halogen, more preferably Br.

Preferably, Q1' is H, methyl or halogen and Q2 is H.

Preferably, the substituted fluorescein stain of formula II is used in an anionic form, preferably in the form of a salt formed with a cation. Preferably, the cation is sodium ion, potassium ion or ammonium ion. According to a further preferred variation, the cation is formed by the bis-3,7 diaminophenothiazine stain of formula I.

Preferably, the chromogenic medium of the invention comprises the at least one type of substituted or unsubstituted bis-3,7 diaminophenothiazine stain and the at least one type of substituted fluorescein stain in essentially identical molar amounts, i.e. the amount of the at least one type of substituted or unsubstituted bis-3,7 diaminophenothiazine stain and the amount of the at least one type of substituted fluorescein stain in the culture medium are at most 50% or 30%, preferably at most 20% or 10% different relative to the component that is present in smaller amount, that is, the ratio of the molar amounts is from 1.5:1 to 1:1 or from 1.3:1 to 1:1, preferably from 1.2:1 to 1:1 or from 1.1:1 to 1:1, most preferably the rate of the molar amounts is 1:1 or vice versa.

Most preferably, the culture medium of the invention contains multiple types of substituted or unsubstituted bis-3,7 aminophenothiazine stains, in the general formula I of which R1, R2, R3 and R4 are H, methyl or ethyl so as that the substituents R1, R2, R3 and R4 are different in the different stains (R1, R2, R3 and R4 may not be identical). Most preferably, R1, R2, R3 and R4 are H or methyl and the bis-3,7 diaminophenothiazine component stains are different in the degrees of methylation.

Accordingly and preferably, methylene blue and the demethylated intermediers thereof or the mixture thereof may be used in the stain, selected from a 3,7-bis(dimethylamino)-phenothiazin-5-ium salt, preferably acetate or chloride (methylene blue), a N-methyl,N',N'-dimethylphenothiazin-5-ium-3,7-diamine salt, preferably acetate or chloride (Azure B), a N',N'-dimethylphenothiazin-5-ium-3,7-diamine salt, preferably acetate or chloride (Azure A: CAS 531 533)

a N-methylphenothiazin-5-ium-3,7-diamine salt, preferably acetate or chloride (Azure C), a phenotiazin-5-ium-3,7-diamine salt, preferably chloride or acetate (thionine).

Most preferably the mixture of Azure B and methylene blue is present in the stain.

Chemical formula of methylene blue:

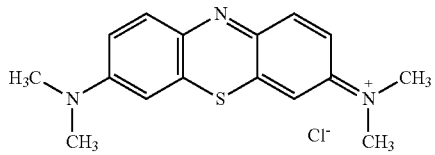

Similarly, the substituted fluoresceins may be of one or more types. Most preferably, an eosin stain or a mixture of eosin stains is used, which may preferably comprise for example Eosin B or Eosin Y.

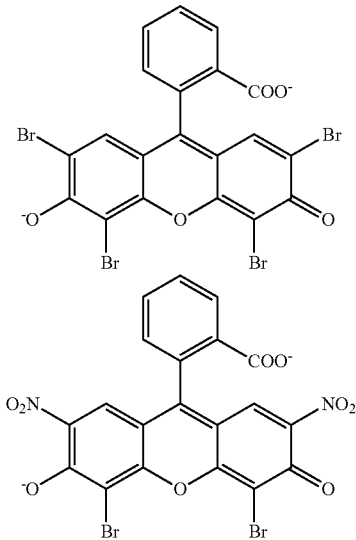

The eosin stain is preferably Eosin B or Eosin Y, the formulas of which are, respectively

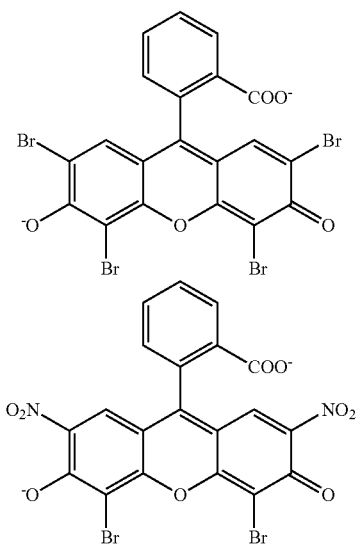

Most preferably, the stain used according to the invention is Azure II eosinate. Azure II eosinate (CAS 53092-85-6) is a mixture of methylene blue and Azure B in the ratio of 1:1 and of eosin Y. Azure II eosinate is available from various manufacturers (such as Fluka, Sinopharm, CN és Nile Chemicals, Ind.).

It is apparent for the skilled artisan that further substituted variants or salts of the stains of the inventions may be used, provided they are chromatic and the colour changes in the presence of yeast.

Considering growth media, any growth medium being suitable for culturing yeasts and containing at least an agent which inhibits the growth of *Saccharomyces* strains can be used, e.g. growth media disclosed in the background of the invention.

Based on the above, the invention concerns a method for selective culturing of *Brettanomyces/Dekkera* yeasts and differential staining of their colonies, where a growth medium suitable for culturing yeast cells is prepared, which is made selective by the addition of an appropriate chemotherapeutic agent or antibiotic inhibiting the growth of *Saccharomyces* strains and by the addition of chromogenic stain of the invention.

The culture medium may be of varied composition. Theoretically, any growth medium suitable for culturing yeasts is appropriate and known by a person skilled in the art. The growth medium preferably contains ingredients selected from the following group: sugar, e.g. glucose; aminoacid- or peptid-containing extract or hydrolizate, such as pepton, yeast extract, "yeast nitrogen base" or "yeast carbon base; geling agent, e.g. agar; and optionally salt. Highly preferably, the growth medium comprises glucose, yeast nitrogen base and agar.

Additionally, the growth medium also contains substances inhibiting the reproduction of microbes having a role in the normal or healthy fermentation of foodstuff. Provided the foodstuff in which the detection method is performed is a foodstuff prepared by fermentation, the growth-inhibiting substance feasibly prevents the growing of microorganisms performing the natural fermentation of the foodstuff, e.g. it blocks the growing of noble yeast. It is obvious for a person skilled in the art that the growth inhibitor should be applied at least in such a concentration which is already sufficient enough to block the growth of such microorganisms. At the same time the inhibitor concentration may have an upper threshold not to inhibit the growth of yeasts, the presence of which is desired to be tested. Preferably, the foodstuff is a foodstuff fermented by *Saccharomyces* species, such as beer, wine or other yeast containing product or intermediate, and the agent inhibiting the growth of *Saccharomyces* strains is an appropriate chemotherapeutic agent or antibiotic, e.g. cycloheximide applied in a concentration, e.g. of 0.5-50 µg/ml, preferably 1-20 µg/ml, particularly preferably 2-10 µg/ml, highly preferably something like 5 µg/ml, thereby the selectivity of the growth medium is enhanced or it is made selective.

The sample may be any sample used in the production of such foodstuff, e.g. a sample taken from devices used in the process or a sample drawn from the liquid used for cleaning the devices.

The prepared culture medium is brought to a form suitable for sample application. According to a certain variation a gel is prepared and a plate is poured into, e.g., a Petri dish. Alternatively, any other solid (e.g., in a form of gel) culture medium can be applied where the sample can be plated and the progeny (e.g. colonies) of a single cell can be separated.

In addition to Petri dishes any other culturing container having large surface can be preferably used, where the sample can be spread on the surface of medium formed in it, and it can be closed (e.g., has a lid) and in which the microorganism colonies can be detected and feasibly visualized. It is preferable for the culturing container to be made of glass or plastic, more preferably plastic, and preferably it has a transparent lid.

Kolle dishes or Roux flaks may also be used, they also have large surfaces but the sample should be introduced into the dish through a small opening and performing uniform plating also presents difficulties. Then the opening should be closed in a way that allows some aeration but the sample does not get uncontaminated.

Consequently, according to the invention, sterilisable culturing dishes with lid may be used, in which samples to be tested can be plated on a large surface.

From the samples (e.g., water used for washing barrels or other surfaces) or from their suitable dilutions a predetermined amount is plated on the surface of culture media then they are incubated at 10-37° C., preferably at 20-30° C., particularly preferably at room temperature for about 5-20 days, preferably for 8-16 days, and highly preferably for 10-14 days. It is obvious for a person skilled in the art that the incubation time is necessarily longer at lower temperatures.

On culture medium prepared according to the invention, *Saccharomyces* yeasts stop growing, and the colour of *Brettanomyces/Dekkera* colonies become pink and they can be discriminated from microorganisms which are not harmful or just slightly harmful to the wine. The results are evaluated visually. In the event of sample application, the result can be made quantitative by giving the number of cultivable yeast cells per 1 ml.

Detection sensitivity of *Brettanomyces/Dekkera* yeasts may be enhanced by filtering a higher amount of wine through membranes with 0.45 μm or 0.22 μm pore size, then by placing the membrane on the surface of the culture medium. In this case it should be ensured that no air bubbles are present between the membrane and the agar surface.

Furthermore, the invention relates to culture media for performing the above method where the medium is in a powder or in a ready-to-use form, and also to the kits containing them and other components necessary for performing the examination (e.g. sample application devices) and the user instructions as well. Preferably, the reagent kit of the invention comprises the culture medium necessary for performing the method of the invention in the form and amount pre-weighed for each test and in a form poured into plastic Petri dishes in advance.

The method developed by us is cheap and it does not require special instrumentation and easy to perform by anyone. The procedure requires no sterile laboratory conditions and only little attention is to be paid to ensure that the right sample is placed on the surface of the culture medium. The culture medium contains components easily available. In addition to components used for growth, the medium contains antibiotics inhibiting the growth of yeasts, e.g.— other culture media similar to selective *Brettanomyces*— cycloheximide as well. This antibiotic is used for the identification of different species in yeast diagnostics. In the concentration used by the inventors, it prevents the growth of most yeasts playing a role in wine-making (e.g. *Saccharomyces*) while this concentration is still tolerated by the species causing the degradation of wine.

The present invention is further illustrated, but not limited by the following examples.

EXAMPLES

In the following examples, unless indicated otherwise, the following concentrations and compositions were applied. Composition of medium that was suitable for growing yeast cells was the following: 1% glucose, 0.67% "yeast nitrogen base", 2% agar, which was made selectively by using 5 μg/ml cycloheximide as an antibiotics for blocking the growth of *Saccharomyces* strains. Azure-II-eosinate was used in a 30 μg/ml concentration.

Example 1: Identifying *Brettanomyces/Dekkera* Species from Must

We make a 10 scale dilution sequence in 5 steps from destilled water that we gained from must. From each dilution we streak 50 μl onto the surface of the selective, chromogen medium in the Petri dishes. We make the grafting in three parallel running measurements. We incubate the Petri dishes between 20-25° C. for 10-14 days. The pink colonies that appear on the surface of the medium after the incubation time is over imply the *Brettanomyces/Dekkera* infection. We choose the dishes in which we can easily identify the number of colonies. If we multiply the number of colonies by twenty, plus the value of the dilution we get the plate count of the *Brettanomyces/Dekkera* of the must applied to 1 ml.

A positive dish can be examined under UV light as well. The fluorescence of the colonies confirms the obtained results.

Example 2: Identifying *Brettanomyces/Dekkera* Species from Bottled Wine

We shake up the wine before taking a sample, then we filtrate 500 ml of it through a membrane filter with 0.45 μm pore diameter. We place the membrane filter on the surface of the selective chromogenic medium in the Petri dish, in a way that it fits properly (there should be no air bubble between them). The Petri dishes are incubated on 20-25° C. for 10-14 days.

Example 3: Identifying *Brettanomyces/Dekkera* Species From Red Wine Stored in Barrels We centrifugate 50 ml from the red wine in the barrel (3000 rpm, 10 min, Hereus Multifuge 3S). We suspend the pellet in 1 ml destilled water. From the suspension we streak 100 μm on the surface of the selective chromogenic medium in the Petri dish. The Petri dishes are incubated on 20-25° C. for 10-14 days.

Example 4: Identifying *Brettanomyces/Dekkera* Species from Barrels

After washing the barrels, we filtrate 500 ml from the wash water through a membrane filter with 0.45 μm pore diameter. We place the membrane filter on the surface of the selective chromogenic medium in the Petri dish, in a way that it fits properly (there should be no air bubble between them). The Petri dishes are incubated on 20-25° C. for 10-14 days.

Example 5: Identifying *Brettanomyces/Dekkera* Species from Grapes

We gently shake the grapes that are soaked in destilled water for an hour on room temperature. Meanwhile the cells from the grapes are being washed in the water. After this, we pour out the water from the grapes and filtrate it through a membrane filter with 0.45 µm pore diameter. We place the membrane filter on the surface of the selective chromogenic medium in the Petri dish, in a way that it fits properly (there should be no air bubble between them). The Petri dishes are incubated on 20-25° C. for 10-14 days.

Example 6: Identifying *Zygosaccharomyces bailii* from Bottled Sweet Wines

We filtrate 500 ml from the bottled sweet wine through a membrane filter with 0.45 µm pore diameter. We place the membrane filter on the surface of the selective chromogenic medium in the Petri dish, in a way that it fits properly (there should be no air bubble between them). The Petri dishes are incubated on 30° C. for 10-14 days. The appearing blue colonies show a positive result.

Example 7: Identifying the Level of Infectivity of Collective Strains of *Brettanomyces/Dekkera, Zygosaccharomyces Bailii* and *Lachancea fermentatii*

We suspend 1 loop from the culture in 5 ml destilled water. From the suspension we streak it on the surface of the differentiating medium with the loop. The Petri dishes are incubated on 20-25° C. for 10-14 days. The appearing blue *Zygosaccharomyces bailii* colonies, the pink *Brettanomyces/Dekkera*, and the greenish blue *Lachancea fermentatii* with the pink edge indicate infection.

Example 8: Recovering Pure Culture of *Brettanomyces/Dekkera* Strains in Culture Collection We suspend 1 loop of the infected culture in 5 ml destilled water. With the loop we streak on the differentiating medium from the suspension. The Petri dishes are incubated on 20-25° C. for 10-14 days.

We make a suspension from the appearing pink colonies (1 loop/5 ml sterile destilled water), and from the suspension we streak on the differentiating medium with a loop. The Petri dishes are incubated on 20-25° C. for 10 days. If we do not observe other colonies apart from the pink ones, we can be ascertained about the purity of the culture.

Example 9: Testing Other Azure and Eosin Stains (Reference Example)

We conducted the experiment according to example X. with the following stains as well:
Stain
Azure A (Azure A chloride)
Azure B
Azure II
Eosin B
Eosin Y The colour of the applied stains change in each case with the increase of pH. The stains were not suitable for clearly separating the species of *Brettanomyces/Dekkera* from the other, examined yeasts.

Example 10: Testing Media

We conducted the experiment according to example X with the following media:

YPD (1% glucose, 1% pepton, 0.5% yeast extract, 2% agar)
YNB (1% glucose, 0.67% yeast nitrogen base, 2% agar)
YCB (0.5% ammonium sulfate, 1.17% yeast carbon base, 2% agar)

We experienced the most contrasted pink/blue discolouration on YNB medium in case of the azure II-eosin.

INDUSTRIAL APPLICABILITY

The process and the media specified by the invention can be advantageously applied in the first place to monitor cell counts of *Brettanomyces/Dekkera*, identify or exclude their proliferation, as well as to detect for a hygienic purpose *Brettanomyces/Dekkera* yeasts responsible for the deterioration of wines and provisions in case of utensils used for storage with which they can get directly into contact. The usage of the medium makes the early identification of the growth of *Brettanomyces/Dekkera* yeasts—that can trigger the deterioration of food and wine—possible, as well as verifying the effect of the treatments that are aimed at avoiding deterioration. The method can identify other microorganisms, such as yeast species belonging to the *Zygosaccharomyce* genus and *Lachancea* genus.

An advantage of this method is that it makes it possible to easily identify the colonies of *Brettanomyces/Dekkera* by looking at them, furthermore, colonies of yeast species belonging to the *Zygosaccharomyces* and *Lachancea* genus can be distinguished from the colonies, other species and wild yeasts that are able to grow on a selective medium. The identification that is based on visibility, not only makes the identification process much easier, but it also does not require experience and scent samples, furthermore, it makes scenting samples unnecessary, which bears the possibility of spreading the infection. The reason why it is more specific to *Brettanomyces/Dekkera* species than other methods, is that it is able to identify other yeast species that are not winemaking (noble) yeasts, which causes a problem in case of sweet wines with a higher residue of sugar.

The method that we developed is cheap, it does not require special instruments, anyone can carry it out. Circumstances of a sterile laboratory are not necessary, it only requires minimal attention to put the right sample onto the surface of the medium. The medium contains easily accessible components.

REFERENCES

Barata A., Seborro F., Belloch C., Malfeito-Ferreira M., Loureiro V.: Ascomycetous yeast species recovered from grapes damaged by honeydew and sour rot. Journal of Applied Microbiology, Volume 104, Issue 4, pages 1182-1191

Couto J A, Barbosa A, Hogg T.: A simple cultural method for the presumptive detection of the yeasts *Brettanomyces/Dekkera* in wines. Left Appl Microbiol. 2005; 41(6):505-10.

EP1185686(A1) Loureiro Virgilio Borges; Goncalves Maria Da Graca Alves; Rodrigues Nuno Miguel Sousa Fa. Culture medium for detection of *Dekkera* and *Brettanomyces*

ES 2268970 (A1) Velazquez Perez Encarna; Lopez Rodrigues Da Silva Luis; Trujillo Toledo Martha Estela [Es]; Mateos Gonzalez Pedro Francisc; Martinez Molina Eustoquio. Yeasts detection culture medium comprises glucose mixed with buffer microorganism and bacterial growth inhibitors and e.g. a nitrogen source GB1248197—ABBOTT LAB [US], "Diagnostic method and apparatus for the detection of bacteria"

Hocking A D.: Media for preservative resistant yeasts: a collaborative study. Int J Food Microbiol. 1996; 29(2-3): 167-75.

Jose I. Ibeas, Ignacio Lozano, Francisco Perdigones, and Juan Jimenez: Detection of *Dekkera-Brettanomyces* Strains in Sherry by a Nested PCR Method. Appl. Environ. Microbiol. Mar. 1996, p. 998 1003 Vol. 62, No. 3

Laurie Connell, Henrik Stender, and Charles G. Edwards: Rapid Detection and Identification of *Brettanomyces* from Winery Air Samples Based on Peptide Nucleic Acid Analysis. Am. J. Enol. Vitic. 2002; 53(4): 322-24.

Loureiro V, Malfeito-Ferreira M. Spoilage yeasts in the wine industry. Int J Food Microbiol. 2003; 86(1-2):23-50.

Luca Cocolin, Kalliopi Rantsiou, Lucilla lacumin, Roberto Zironi, and Giuseppe Comi: Molecular Detection and Identification of *Brettanomyces/Dekkera bruxellensis* and *Brettanomyces/Dekkera anomalus* in Spoiled Wines. Appl Environ Microbiol. 2004; 70(3): 1347-1355.

Mitrakul, C. M., T. Henick-Kling, and C. M. Egli: Discrimination of *Brettanomyces/Dekkera* yeast isolates from wine by using various DNA fingerprinting methods. Food Microbiol. 1999; 16:3-14.

Renouf V, Lonvaud-Funel A.: Development of an enrichment medium to detect *Dekkera/Brettanomyces bruxellensis*, a spoilage wine yeast, on the surface of grape berries. Microbiol Res. 2007; 162(2): 154-67.

Rodrigues N, Gonçalves G, Pereira-da-Silva S, Malfeito-Ferreira M, Loureiro V. Development and use of a new medium to detect yeasts of the genera *Dekkera/Brettanomyces*. J Appl Microbiol. 2001; 90(4):588-99.

Schuller D, Côrte-Real M, Leão C.: A differential medium for the enumeration of the spoilage yeast *Zygosaccharomyces bailii* in wine. J Food Prot. 2000; 63(11):1570-5.

Stender, H., C. Kurtzman, J. J. Hyldig-Nielsen, D. Sorensen, A J. Broomer, K. Oliveira, H. Perry-O'Keefe, A. Sage, B. Young, and J. Coull: Identification of *Dekkera bruxellensis* (*Brerranomyces*) from wine by fluorescence in situ hybridization using peptide nucleic acid probes. Appl. Environ. Microbiol. 67:938-941 (2001).

Trevor G. Phister and David A. Mills: Real-Time PCR Assay for Detection and Enumeration of *Dekkera bruxellensis* in Wine. Applied and Environmental Microbiology. 2003; 69(12):7430-7434.

WO0073494 (A1) Leao Cecilia; Corte-Real Manuela; Schuller Dorit

The invention claimed is:

1. A chromogenic medium suitable for the selective growth and detection of one or more yeast(s) from a yeast of the *Brettanomyces* and/or *Dekkera* genera, a yeast of the *Zygosaccharomyces* genus, and/or a yeast of the *Lachancea* genus, said medium comprising
   at least a nutrient suitable for the feeding and/or growing of said one or more yeast(s) to be detected,
   an agent capable of inhibiting the growth of *Saccharomyces* species, and
   a chromogenic stain, wherein the chromogenic stain is the combination of the following dyes, said combination being chromatic under visible light:
      multiple type(s) of substituted and/or unsubstituted bis-3,7 diaminophenothiazines comprising a mixture of methylene blue and Azure B, and
      one or multiple type(s) of substituted fluorescein(s),
   wherein the substituted fluorescein is selected from the group consisting of eosin Y, eosin B and any mixture thereof.

2. The selective and chromogenic medium according to claim 1, wherein said chromogenic stain comprises the mixture of methylene blue and Azure B, and of Eosin Y.

3. The selective and chromogenic medium according to claim 2 wherein said chromogenic stain is Azure II eosinate.

4. The selective and chromogenic medium according to claim 1, wherein said chromogenic stain is a mixture of
   the bis-3,7 diaminophenothiazines consisting of a mixture of methylene blue and Azure B and
   the one or multiple type(s) of substituted fluorescein(s) in the ratio of from 1.5:1 to 1:1.

5. The selective and chromogenic medium according to claim 1, comprising a gelling agent and being formulated as one of the following forms:
   solid powder, gelled culture medium,
   wherein
   the medium is in a pre-prepared, ready to use form.

6. The chromogenic medium of claim 1 which is a culture medium for said one or more yeast(s) to be detected.

7. The chromogenic medium of claim 1, wherein said agent is at a concentration which does not inhibit growth the one or more yeast(s) to be detected.

8. The chromogenic medium of claim 1, wherein the nutrient in the medium is capable of feeding said one or more yeast(s) to be detected.

9. The chromogenic medium of claim 1 further comprising water.

10. The chromogenic medium of claim 1, wherein the one or more yeast(s) to be detected is/are capable of naturally growing in said medium.

11. The chromogenic medium of claim 1 further comprising glucose, yeast nitrogen base and agar.

12. The chromogenic medium of claim 1, wherein said agent is a chemotherapeutic agent or an antibiotic.

13. A method for the detection or determination of one or more yeast species selected from the group as follows: yeasts of the *Brettanomyces* and/or *Dekkera* genera, yeasts of the *Zygosaccharomyces* genus, and yeasts of the *Lachancea* genus, from a foodstuff, a food processing intermediate and/or a food raw material, said method comprising the steps of
   providing the medium of claim 1,
   obtaining a sample from a foodstuff, a food processing intermediate and/or a food raw material,
   preparing the sample to add to the medium, optionally filtering and/or concentrating and/or enriching the sample in microorganisms,
   plating the sample or suitable part thereof on the medium,
   incubating the medium under conditions suitable for the culturing of said yeast species until colonies are obtained,
   detecting said yeast species by the discolouration of said colonies.

14. The method of claim 13, wherein said yeast is selected from a yeast of the *Brettanomyces* and/or *Dekkera* genera, a yeast species of the *Zygosaccharomyces* genus and a yeast species of the *Lachancea* genus, and
   when the colony is pink, it is considered to be the detection of a yeast of the *Brettanomyces* and/or *Dekkera* genera, and/or
   when the colony is blue, it is considered to be the detection of a yeast species of the *Zygosaccharomyces* genus, and/or
   when the colony is greenish blue with a pink edge, it is considered to be the detection of a yeast species of the *Lachancea* genus.

15. The method according to claim 13, wherein the number of detected colonies is determined relative to the amount of the volume or weight of the original sample, so that the method is quantitative.

16. The method according to claim 13, wherein the colonies and the number of the colonies are evaluated under UV light, by fluorescence.

17. The method according to claim 13, wherein the foodstuff prepared by fermentation, is beer or wine, the food processing intermediate is malt, must, fermenting malt or must, and/or the food raw material is grape.

18. The method according to claim 13, wherein the culture medium suitable for the culturing of said yeast is provided in a pre-prepared, ready to use solid or gel form.

19. Kit for use in the method according to claim 13 containing the medium and means of preparing a gel culture medium thereof.

\* \* \* \* \*